(12) United States Patent
Wang et al.

(10) Patent No.: US 10,278,752 B2
(45) Date of Patent: May 7, 2019

(54) BONE NAIL APPARATUS

(71) Applicants: KAOHSIUNG MEDICAL UNIVERSITY, Kaohsiung (TW); NATIONAL SUN YAT-SEN UNIVERSITY, Kaohsiung (TW)

(72) Inventors: Jau-Sheng Wang, Keelung (TW); Tien-Ching Lee, Kaohsiung (TW); Mei-Ling Ho, Kaohsiung (TW); Yin-Chih Fu, Kaohsiung (TW); Wei-Chi Chen, Taichung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 214 days.

(21) Appl. No.: 15/293,283

(22) Filed: Oct. 14, 2016

(65) Prior Publication Data

US 2017/0105777 A1    Apr. 20, 2017

(30) Foreign Application Priority Data

Oct. 16, 2015   (TW) .............................. 104134065 A

(51) Int. Cl.
| | | |
|---|---|---|
| *A61B 17/72* | (2006.01) | |
| *A61B 17/84* | (2006.01) | |
| *A61B 17/17* | (2006.01) | |
| *A61B 90/30* | (2016.01) | |
| *A61B 17/90* | (2006.01) | |

(52) U.S. Cl.
CPC ........ *A61B 17/846* (2013.01); *A61B 17/1725* (2013.01); *A61B 17/72* (2013.01); *A61B 17/7233* (2013.01); *A61B 90/30* (2016.02); *A61B 17/1703* (2013.01); *A61B 17/1707* (2013.01); *A61B 2017/90* (2013.01)

(58) Field of Classification Search
CPC ....................................... A61B 17/72–17/8695
See application file for complete search history.

(56) References Cited

U.S. PATENT DOCUMENTS

| | | | | |
|---|---|---|---|---|
| 4,621,628 A | * | 11/1986 | Brudermann | ...... A61B 17/1707 606/64 |
| 5,002,532 A | * | 3/1991 | Gaiser | ................ A61M 25/1011 604/101.01 |
| 5,411,503 A | * | 5/1995 | Hollstien | ........... A61B 17/1707 606/80 |
| 5,417,688 A | * | 5/1995 | Elstrom | ............. A61B 17/1703 601/3 |

(Continued)

*Primary Examiner* — Zade Coley
(74) *Attorney, Agent, or Firm* — Hannah Tien

(57) ABSTRACT

A bone nail apparatus includes a bone nail, a light source unit and a focalizing unit. The bone nail has a tube wall and at least one through hole. The tube wall is enclosed to form a receiving space. The at least one through hole extends through the tube wall and communicates with the receiving space. The light source unit includes a light emitter and at least one light transmission tube. The at least one light transmission tube is connected to the light emitter and receives a light therefrom. The at least one light transmission tube is received in the receiving space of the bone nail. Each light transmission tube has a light-outputting end aligned with a respective one of the at least one through hole. The focalizing unit has a light-receiving face facing one of the at least one through hole.

6 Claims, 4 Drawing Sheets

(56) References Cited

U.S. PATENT DOCUMENTS

| | | | | |
|---|---|---|---|---|
| 5,993,456 | A * | 11/1999 | Speitling | A61B 17/164 606/64 |
| 6,081,741 | A * | 6/2000 | Hollis | A61B 17/1703 600/424 |
| 2007/0177009 | A1 * | 8/2007 | Bayer | A61B 1/00096 348/65 |
| 2007/0270864 | A1 * | 11/2007 | Gurtowski | A61B 5/0084 606/79 |
| 2010/0274256 | A1 * | 10/2010 | Ritchey | A61B 5/05 606/96 |
| 2013/0258458 | A1 * | 10/2013 | Hogele | G02B 21/025 359/380 |
| 2014/0163557 | A1 * | 6/2014 | Beyar | A61B 17/1703 606/80 |

* cited by examiner

BONE NAIL APPARATUS

CROSS REFERENCE TO RELATED APPLICATIONS

The application claims the benefit of Taiwan application serial No. 104134065, filed on Oct. 16, 2015, and the subject matter of which is incorporated herein by reference.

FIELD OF THE INVENTION

The present disclosure generally relates to a bone nail apparatus and, more particularly, to a bone nail apparatus that can be fixed in place through the transmitted light.

BACKGROUND OF THE INVENTION

Skeleton is an important structure of the human body. When a bone breaks, a bone nail is often inserted into the bone. Then, a plurality of screws is inserted into the bone and extended through the through-holes of the bone nail. As such, the bone nail can be fixed in the bone to provide a supporting mechanism for the human body and to maintain the normal structure and shape of the fractured bone.

In general, after the bone nail is inserted into the bone, the locations of the through-holes of the bone nail can no longer be determined by the eyes from outside of the body. In light of this, the conventional bone nail was provided with a light-emitting element that is aligned with the through-holes of the bone nail. Therefore, after the bone nail is inserted in the bone, the positions of the through-holes of the bone nail can be located via the outgoing light that emits outwardly from the through-holes of the bone nail.

However, a portion of the light will be refracted or scattered as the light emits through the bone and the skin, thus changing its transmission direction and forming the halos on the surface of the skin. Since the sizes of the halos do not correspond to the diameters of the through-holes of the bone nail, it is still unable to preciously determine the locations of the through-holes via the halos. As a result, the accuracy in determining the locations of the through-holes is not high.

In light of this, it is necessary to provide a bone nail apparatus that can be fixed in place more conveniently.

SUMMARY OF THE INVENTION

The present invention relates to a bone nail apparatus including a bone nail, a light source unit and a focalizing unit. The bone nail has a tube wall and at least one through hole. The tube wall is enclosed to form a receiving space. The at least one through hole extends through the tube wall and communicates with the receiving space. The light source unit includes a light emitter and at least one light transmission tube. The at least one light transmission tube is connected to the light emitter and receives a light therefrom. The at least one light transmission tube is received in the receiving space of the bone nail. Each light transmission tube has a light-outputting end aligned with a respective one of the at least one through hole. The focalizing unit has a light-receiving face facing one of the at least one through hole.

BRIEF DESCRIPTION OF THE DRAWINGS

The present disclosure will become more fully understood from the detailed description given hereinafter and the accompanying drawings which are given by way of illustration only, and thus are not limitative of the present disclosure, and wherein.

Figure 1:
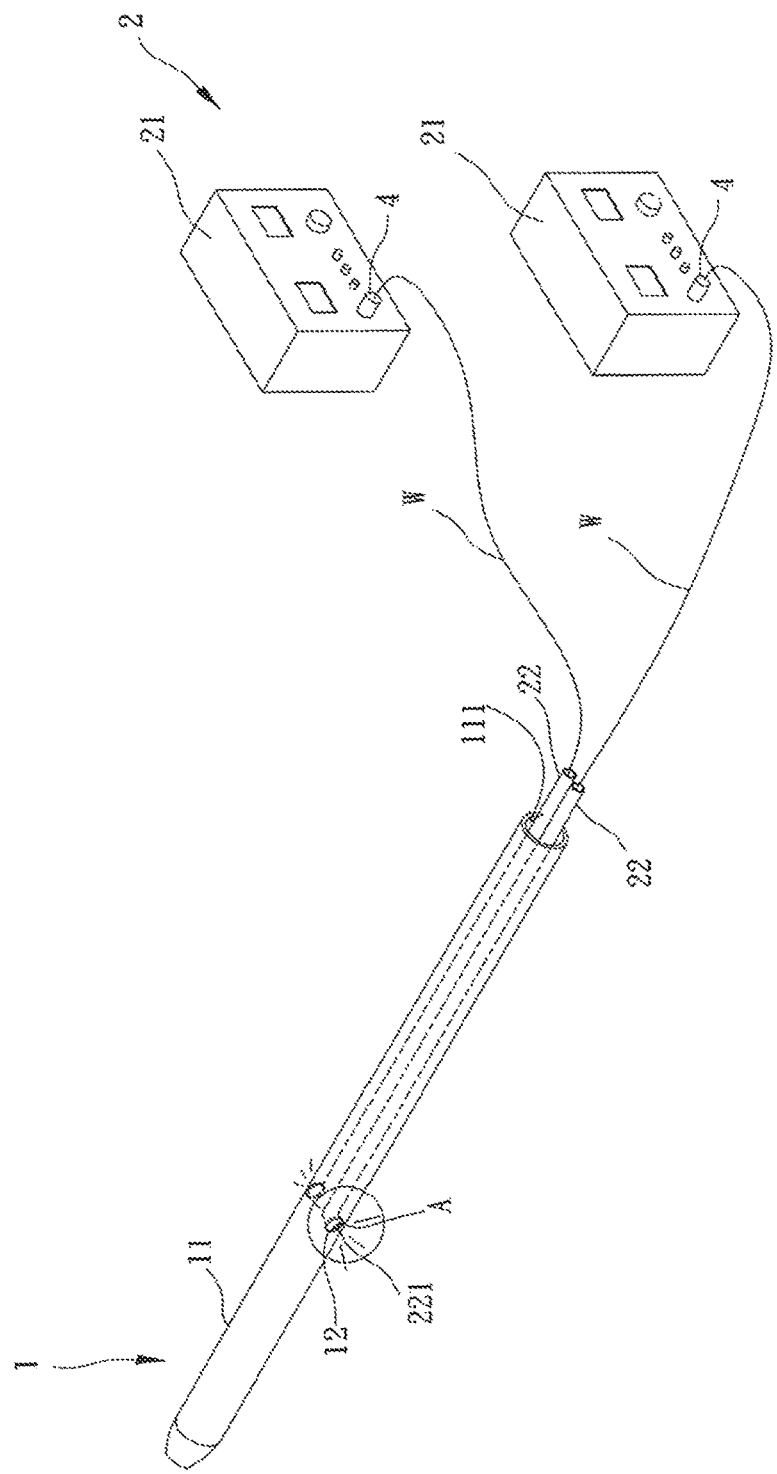
FIG. 1 shows a bone nail apparatus according to an embodiment of the disclosure.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the disclosure.

DETAILED DESCRIPTION OF THE INVENTION

It is therefore the objective of this disclosure to provide a bone nail apparatus whose through holes can be preciously located.

In an embodiment of the disclosure, a bone nail apparatus including a bone nail, a light source unit and a focalizing unit is disclosed. The bone nail has a tube wall and at least one through hole. The tube wall is enclosed to form a receiving space. The at least one through hole extends through the tube wall and communicates with the receiving space. The light source unit includes a light emitter and at least one light transmission tube. The at least one light transmission tube is connected to the light emitter and receives a light therefrom. The at least one light transmission tube is received in the receiving space of the bone nail. Each of the at least one light transmission tube has a light-outputting end aligned with a respective one of the at least one through hole. The focalizing unit has a light-receiving face located outside of the bone nail and facing one of the at least one through hole. As such, the determination on the position(s) of the at least one through hole can be improved.

In a form shown, each of the at least one through hole has a periphery applied with a sealing adhesive, and the light-outputting end of each of the at least one light transmission tube is adhered to and aligned with the respective one of the at least one through hole via the sealing adhesive. As such, the engaging effect between the at least one light transmission tube and the at least one through hole can be improved.

In the form shown, the focalizing unit includes a concave lens forming a light-receiving face. As such, the determination on the position(s) of the at least one through hole can be improved. In the form shown, the light source is a laser emitting light source, or a light source that can control the laser emitting interval to avoid surgery damage which is probably caused by consistently lighting at a same spot.

In the form shown, the focalizing unit includes a fixed support, and the concave lens is arranged on the fixed support. As such, the positioning effect of the concave lens can be improved.

In the form shown, the fixed support has a positioning ring, and wherein the concave lens is positioned by the positioning ring. As such, the positioning effect of the concave lens can be improved.

In the form shown, the focalizing unit includes a supporting member coupled with the fixed support. As such, the retaining effect of the fixed support and the utility of the bone nail apparatus can be improved.

In the form shown, the bone nail apparatus further includes at least one filtering unit. Each of the at least one light transmission tube is connected to the light emitter via a respective one of the at least one filtering unit. As such, the determination on the position(s) of the at least one through hole can be improved.

In the form shown, each of the at least one filtering unit is a light filter adapted to filter polarized lights. As such, the determination on the position(s) of the through hole can be improved.

In the form shown, each of the at least one filtering unit is a light attenuator. As such, the determination on the position(s) of the through hole can be improved.

Based on the above, the bone nail apparatus of the embodiment of the disclosure is able to focus the dispersed light on a focal point, thereby improving the accuracy in determining the position(s) of the at least one through hole.

EXAMPLES

Figure 3:
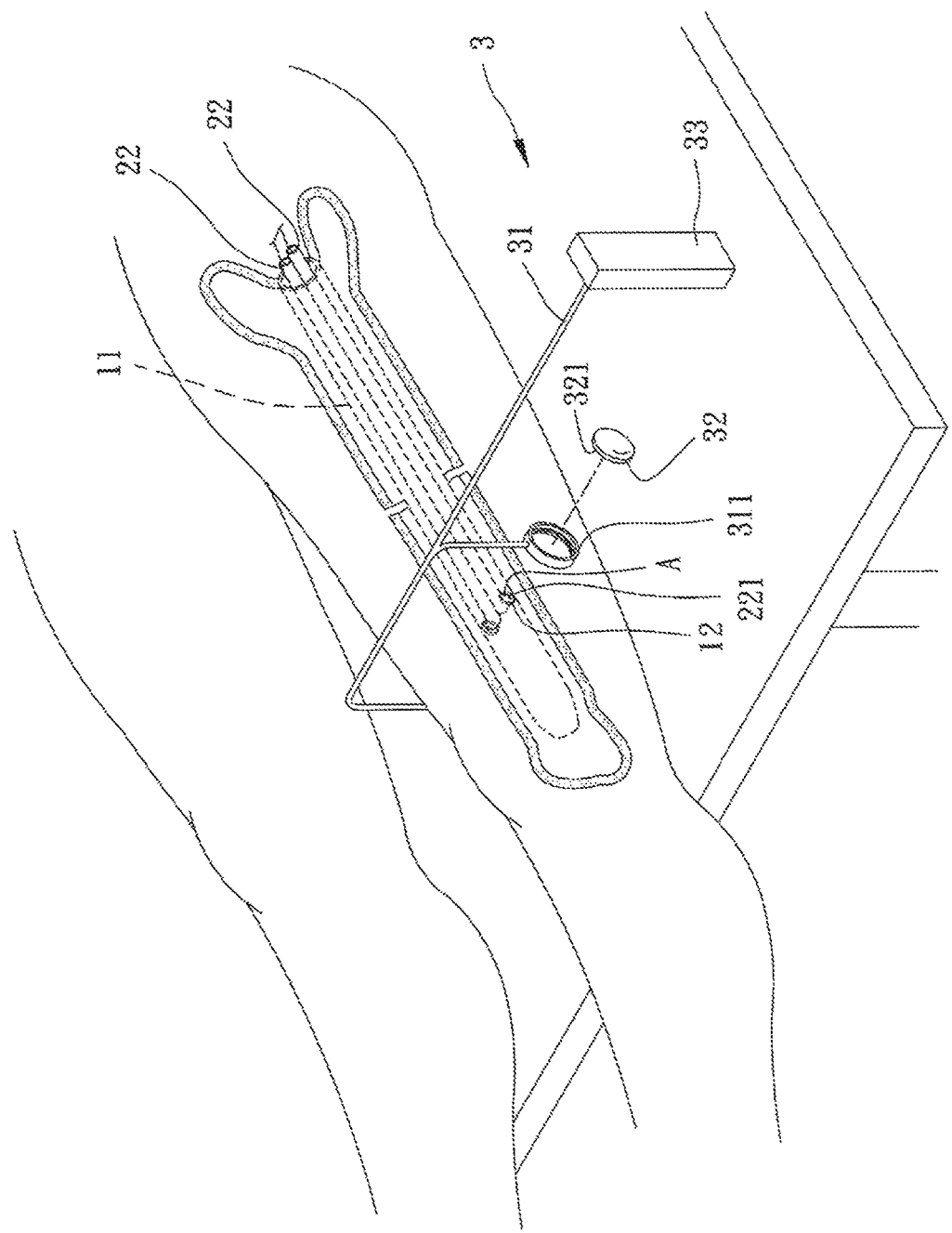
FIG. 3 shows the use of the bone nail apparatus of the embodiment of the disclosure.

FIG. 1 shows a bone nail apparatus having a bone nail 1, a light source unit 2, and a focalizing unit 3, that is shown in FIG. 3. The light source unit 2 is partially received in the bone nail 1, and the focalizing unit 3 is located outside of the bone nail 1.

The bone nail 1 includes a tube wall 11 and at least one through hole 12. The tube wall 11 is enclosed to form a receiving space 111. The at least one through hole 12 extends through the tube wall 11 and communicates with the receiving space 111.

Specifically, the bone nail 1 is in the form of a hollow tube, and the at least one through hole 12 is arranged between two ends of the tube. The at least one through hole 12 may include a single through hole 12, two through holes 12 as is the case in the embodiment, or more than two through holes 12.

The light source unit 2 includes at least one light emitter 21 and at least one light transmission tube 22. The at least one light transmission tube 22 is coupled with the at least one light emitter 21 for receiving a light therefrom. The at least one light transmission tube 22 is received in the receiving space 111 of the bone nail 1. Each of the at least one light transmission tube 22 has a light-outputting end 221 for outputting the light. The light-outputting end 221 is aligned with a respective one of the at least one through hole 12.

Specifically, the emitted light of the light emitter 21 preferably has a wavelength from 600 nm to 1500 nm. The light, such as visible light or near infrared ray, is able to penetrate the skin and the bone of the human body. Each of the least one light emitter 21 can be connected to a respective one of the at least one light transmission tube 22 via a transmission line "W." The transmission tube 22 may be inserted into the receiving space 111 via one end of the bone nail 1. The at least one light transmission tube 22 and the at least one through hole 12 are preferably in the same quantity. For example, in the embodiment, the quantity of the at least one light transmission tube 22 is two, and the quantity of the at least one through hole 12 is also two. As such, each of the two light transmission tubes 22 can be aligned with a respective one of the two through holes 12, thereby maintaining the light-outputting stability of each through hole 12 via the use of the light transmission tube 22. However, the quantity of the least one light emitter 21 is not limited. The at least one light emitter 21 may include only one light emitter 21 that is connected to one or more light transmission tubes 22. In one embodiment, there are two light emitters 21 connected to two light transmission tubes 22, respectively. The light transmission tube 22 may be any device capable of transmitting the light, such as a fiber. The fore end of the fiber could be equipped with a lens to guide the fiber into tissues, and improve the positioning accuracy.

Figure 2:
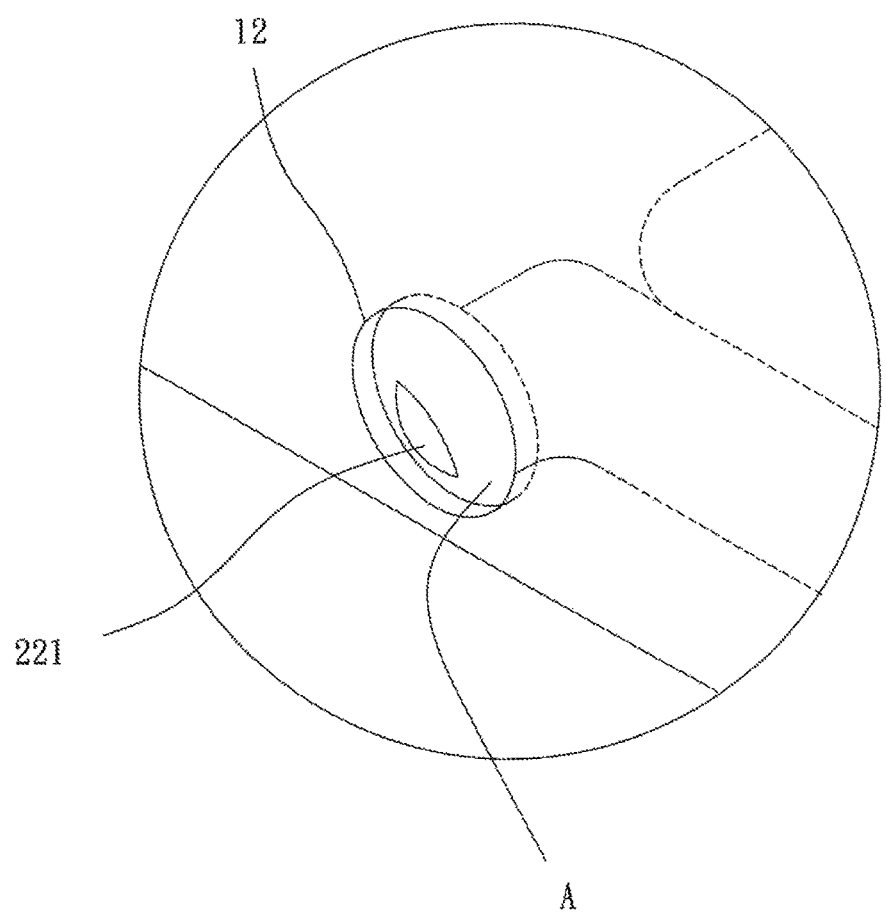
FIG. 2 is a partially enlarged view of the bone nail apparatus according to an embodiment of the disclosure.

Referring to FIGS. 1 and 2, each of the two light-outputting ends 221 of the light transmission tubes 22 may be press fitted by the periphery of a respective one of the two through holes 12. In this regard, each of the two light-outputting ends 221 of the light transmission tubes 22 may be aligned with a respective one of the two through holes 12. In addition, each of the two light transmission tubes 22 may abut an inner face of the tube wall 11, such that a long needle (not shown in the figures) that is used to guide the bone nail 1 can be placed in the receiving space 111. Thus, the light transmission tubes 22 will not be pulled by the needle extending into the receiving space 111, and the positioning of the light transmission tubes 22 will not be affected. Furthermore, when the light transmission tubes 22 are not adhered to the through holes 12, the light transmission tubes 22 may be fixed to the needle so that the light transmission tubes 22 can be guided by the needle to move back and forth (as is in a telescopic manner of a probe). Alternatively, the periphery of each through hole 12 is applied with a sealing adhesive "A" in the embodiment, and the light-outputting end 221 of each of the two light transmission tubes 22 is adhered to a respective one of the two through holes 12 via the sealing adhesive "A." Thus, the light-outputting end 221 of each of the two light transmission tubes 22 can be aligned with a respective one of the two through holes 12. As such, the sealing adhesive "A" can fill the gap between the outer face of the light-outputting end 221 and the periphery of the through hole 12, thus securely fixing the light-outputting end 221 of each of the two light transmission tubes 22 in the through hole 12. Advantageously, the light-outputting end 221 of each of the two light transmission tubes 22 can be stably positioned in a respective one of the two through holes 12. As such, the determination on the position(s) between the light transmission tube 22 and the through hole 12 can be improved.

Please refer to FIG. 3, the focalizing unit 3 includes a fixed support 31 and a concave lens 32. The fixed support 31 includes a positioning ring 311. The concave lens 32 forms a light-receiving face 321 on a side thereof. The light-receiving face 321 is located outside of the bone nail 1 and faces the at least one through hole 12.

Specifically, the concave lens 32 is detachably arranged in the positioning ring 311. For instance, the concave lens 32 is detachably arranged in the positioning ring 311 by ways of abutment or engagement. As such, the light-receiving face 321 of the concave lens 32 can be fixed in a position facing the at least one through hole 12, or can also be detached from the positioning ring 311 if required. Therefore, the positioning effect and utility of the concave lens 32 are improved.

Moreover, the focalizing unit 3 includes a supporting member 33 coupled with the fixed support 31. More specifically, the supporting member 33 may be in any form capable of retaining the fixed support 31 or adjusting the height of the fixed support 31. Arrangement of the supporting member 33 improves the positioning effect of the fixed support 31 and the concave lens 32. In addition, the position of the concave lens 32 relative to the through hole 12 may be changed by adjusting the height of the fixed support 31. Thus, the positioning effect and utility of the concave lens 32 can be improved.

Referring to FIG. 1 again, the bone nail apparatus of the embodiment of the disclosure further includes a filtering unit 4. The light transmission tube 22 is connected to the light emitter 21 via the filtering unit 4. The filtering unit 4 may be a light attenuator or a light filter adapted to filter polarized lights.

More specifically, the light is one of the forms of the electromagnetic field whose polarization direction of the electric field occurs at every angle. When a light having a plurality of polarization directions is transmitted through the light transmission tube 22 and emits outwardly from the through hole 12 and passes the bone and skin of the human body, the degree of scattering of the light will increase if the polarization directions of the light are not parallel to the texture of the skin. As a result, a wider range of halos will be formed on the skin, such that the positions of the through holes 12 cannot be determined. Thus, when the filtering unit 4 is a light filter for filtering polarized lights, the light filter preferably filters the light with certain polarization directions. For example, for a light-outputting direction where the light emits outwardly from the light-outputting end 221 of the light transmission tube 22, a portion of the light with the polarization directions unparallel to the skin texture will be filtered out. As such, the degree of scattering of the light passing through the skin can be lowered, thus forming a smaller range of halos on the surface of the skin. Thus, the determination on the locations of the through holes 12 can be more accurate.

Furthermore, when the light that is transmitted through the light transmission tube 22 emits outwardly from the through hole 12 and passes through the bone and skin of the human body, the degree of scattering of the light will be higher if the strength of the light is too large. As a result, it is difficult to determine the locations of the through holes 12 from outside the body based on the halo. Therefore, when the filtering unit 4 is a light attenuator, the light attenuator is able to reduce the strength of the outputted light of the light source unit 2. Advantageously, the strength of the outputted light of the light source unit 2 can be attenuated and the degree of scattering of the light can be reduced, thereby forming a smaller range of halos on the skin surface and improving the accuracy in determining the locations of the through holes 12.

Figure 4:
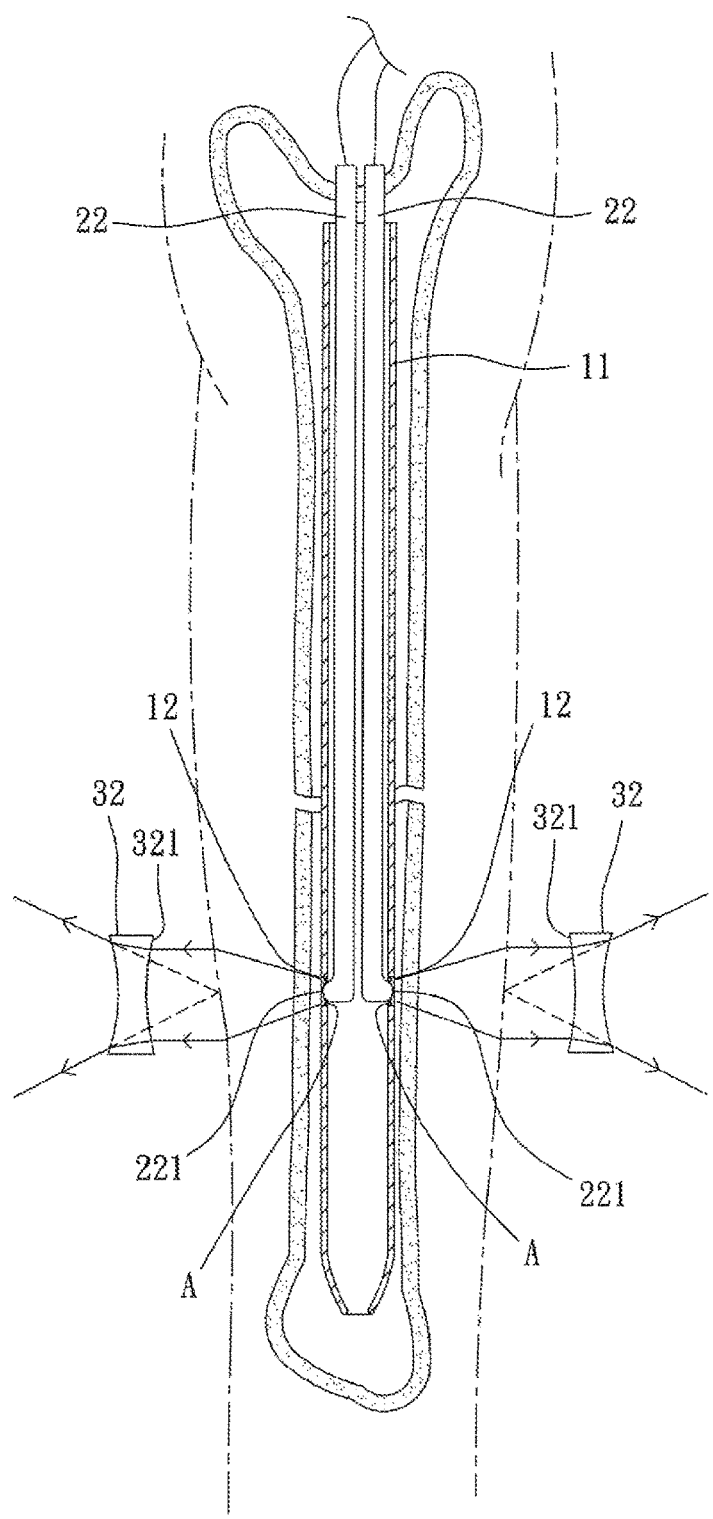
FIG. 4 shows another use of the bone nail apparatus of the embodiment of the disclosure.

Referring to FIGS. 3 and 4, assume there are two through holes 12 and two light transmission tubes 22. In this regard, when the bone nail apparatus of the embodiment of the disclosure is used in an operational treatment of fracture, the bone nail 1 is inserted into a bone of the human body so that the two light-outputting ends 221 of two light transmission tubes 22 are fixed by the sealing adhesive "A" in the positions aligning with two through holes 12. As such, the light is able to emit outwardly from the light-outputting ends 221 of the two light transmission tubes 22 and passes the bone and skin of the human body, forming a predetermined range of halos on the surface of the skin. However, for the light that emits outwardly from the surface of the skin, a certain portion of the light travels in a direction parallel to the light-outputting directions of the two light-outputting ends 221. Therefore, when the light-receiving face 321 of the concave lens 32 faces one of the light-outputting directions, the light that is parallel to the one of the light-outputting directions will diverge toward another face of the light-receiving face 321. The diverged light will converge as a focal point in front of the light-receiving face 321. Based on the focal point, one is able to determine the locations of the two through holes 12 and to extend a screw into the bone at the focal point. As such, the screw can be smoothly inserted into the bone and the two through holes 12, thereby fixing the bone nail 1 in the bone. Therefore, the bone nail apparatus of the disclosure is able to assist the medical staff in accurately locating the through holes 12. Furthermore, when the concave lens 32 is detachably arranged in the positioning ring 311, the concave lens 32 may be removed from the positioning ring 311 after the focal point has been confirmed. In this regard, the screw can be driven into the bone without moving other components of the focalizing unit 3. Thus, a convenient use of the bone nail apparatus is provided. The concave lens 32 may be a double-concave lens. The curvature of the light-receiving face 321 may be flexibly adjusted according to the actual size of the light circles or the distance between the light-receiving face 321 and the surface of the skin, as it can be readily appreciated by the persons skilled in the art.

In conclusion, the bone nail apparatus of the disclosure is able to focus the light on a focal point via the light-receiving face 321 of the focalizing unit 3, in which the location of the focal point on the surface of the skin indicates the relative locations of the through holes 12 in the bone. As such, the through holes 12 can be accurately located.

Although the disclosure has been described in detail with reference to its presently preferable embodiments, it will be understood by one of ordinary skill in the art that various modifications can be made without departing from the spirit and the scope of the disclosure, as set forth in the appended claims.

What is claimed is:

1. A bone nail apparatus comprising:
    a bone nail having a tube wall and at least one through hole, wherein the tube wall is enclosed to form a receiving space, and wherein the at least one through hole extends through the tube wall and communicates with the receiving space;
    a light source unit having a light emitter and at least one light transmission tube, wherein the at least one light transmission tube is connected to the light emitter and receives a light therefrom, wherein the at least one light transmission tube is received in the receiving space of the bone nail, and wherein each of the at least one light transmission tube has a light-outputting end aligned with a respective one of the at least one through hole; and
    a focalizing unit including a light-receiving face located outside of the bone nail and facing one of the at least one through hole; a concave lens forming a light-receiving face on a side thereof; and a fixed support, including a positioning ring, wherein the concave lens is arranged on the fixed support and wherein the concave lens is positioned by the positioning ring configured to allow a user to directly view light advancing through the concave lens.

2. The bone nail apparatus as claimed in claim 1, wherein each of the at least one through hole has a periphery applied with a sealing adhesive, and wherein the light-outputting end of each of the at least one light transmission tube is adhered to and aligned with the respective one of the at least one through hole via the sealing adhesive.

3. The bone nail apparatus as claimed in claim 1, wherein the focalizing unit comprises a supporting member coupled with the fixed support.

4. The bone nail apparatus as claimed in claim 1, further comprising at least one filtering unit, wherein each of the at least one light transmission tube is connected to the light emitter via a respective one of the at least one filtering unit.

5. The bone nail apparatus as claimed in claim 4, wherein each of the at least one filtering unit is a light filter adapted to filter polarized lights.

6. The bone nail apparatus as claimed in claim 4, wherein each of the at least one filtering unit is a light attenuator.

\* \* \* \* \*